United States Patent
Han et al.

(10) Patent No.: US 12,035,074 B1
(45) Date of Patent: *Jul. 9, 2024

(54) PROVIDING DYNAMIC CONTENT TO VIDEO CONFERENCE WAITING ROOMS

(71) Applicant: Zoom Video Communications, Inc., San Jose, CA (US)

(72) Inventors: Lin Han, Los Altos, CA (US); Nitasha Walia, Sunnyvale, CA (US)

(73) Assignee: Zoom Video Communications, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/206,148

(22) Filed: Jun. 6, 2023

Related U.S. Application Data

(63) Continuation of application No. 17/245,186, filed on Apr. 30, 2021, now Pat. No. 11,706,387.

(51) Int. Cl.
*H04N 7/15* (2006.01)
*H04L 12/18* (2006.01)
*H04N 7/14* (2006.01)

(52) U.S. Cl.
CPC ......... *H04N 7/155* (2013.01); *H04L 12/1818* (2013.01); *H04L 12/1822* (2013.01); *H04N 7/14* (2013.01)

(58) Field of Classification Search
None
See application file for complete search history.

(56) References Cited

U.S. PATENT DOCUMENTS

| | | | |
|---|---|---|---|
| 10,264,214 B1 | 4/2019 | Kumar | |
| 11,336,864 B1 | 5/2022 | Han et al. | |
| 11,706,387 B2* | 7/2023 | Walia | G16H 10/20 |
| | | | 348/14.08 |
| 2007/0233291 A1 | 10/2007 | Herde et al. | |
| 2014/0222907 A1 | 8/2014 | Seligmann et al. | |
| 2016/0234264 A1* | 8/2016 | Coffman | H04L 65/403 |
| 2016/0307165 A1 | 10/2016 | Grødum et al. | |
| 2018/0098030 A1 | 4/2018 | Morabia et al. | |
| 2020/0372140 A1 | 11/2020 | Jaber et al. | |
| 2021/0400142 A1* | 12/2021 | Jorasch | H04M 3/567 |

OTHER PUBLICATIONS

U.S. Appl. No. 17/245,186, "Non-Final Office Action", dated Jul. 29, 2022, 8 pages.
U.S. Appl. No. 17/245,186, "Notice of Allowance", dated Mar. 2, 2023, 6 pages.

* cited by examiner

*Primary Examiner* — Quoc D Tran
(74) *Attorney, Agent, or Firm* — Kilpatrick Townsend & Stockton LLP

(57) ABSTRACT

One example method includes receiving, by a video conference provider, an indication of a meeting type of a video conference; obtaining, by the video conference provider, multimedia content associated with the meeting type; receiving a request from a client device to join a main meeting of the video conference; connecting the client device to a waiting room associated with the video conference; and providing the multimedia content to the client device in the waiting room.

20 Claims, 8 Drawing Sheets

US 12,035,074 B1

PROVIDING DYNAMIC CONTENT TO VIDEO CONFERENCE WAITING ROOMS

This application is a continuation application of U.S. patent application Ser. No. 17/245,186, filed Apr. 30, 2021, titled "Providing Dynamic Content to Video Conference Waiting Rooms," the entirety of which is hereby incorporated by reference.

FIELD

Background

Videoconferencing has become a common way for people to meet as a group, but without being at the same physical location. Participants can be invited to a video conference meeting, join from their personal computers or telephones, and are able to see and hear each other and converse largely as they would during an in-person group meeting or event. The advent of user-friendly video conferencing software has enabled teams to work collaboratively despite being dispersed around the country or the world. It has also enabled families and friends to engage with each other in more meaningful ways, despite being physically distant from each other.

SUMMARY

Various examples are described for systems and methods for providing dynamic content to video conference waiting rooms. One example method includes receiving, by a video conference provider, an indication of a meeting type of a video conference; obtaining, by the video conference provider, multimedia content associated with the meeting type; receiving a request from a client device to join a main meeting of the video conference; connecting the client device to a waiting room associated with the video conference; and providing the multimedia content to the client device in the waiting room.

One example system includes a communications interface; a non-transitory computer-readable medium; and one or more processors configured to execute processor-executable instructions stored in the non-transitory computer-readable medium to: receive an indication of a meeting type of a video conference; obtain multimedia content associated with the meeting type; receive a request from a client device to join a main meeting of the video conference; connect the client device to a waiting room associated with the video conference; and provide the multimedia content to the client device in the waiting room.

One example non-transitory computer-readable medium includes processor-executable instructions configured to cause one or more processors to receive an indication of a meeting type of a video conference; obtain multimedia content associated with the meeting type; receive a request from a client device to join a main meeting of the video conference; connect the client device to a waiting room associated with the video conference; and provide the multimedia content to the client device in the waiting room.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
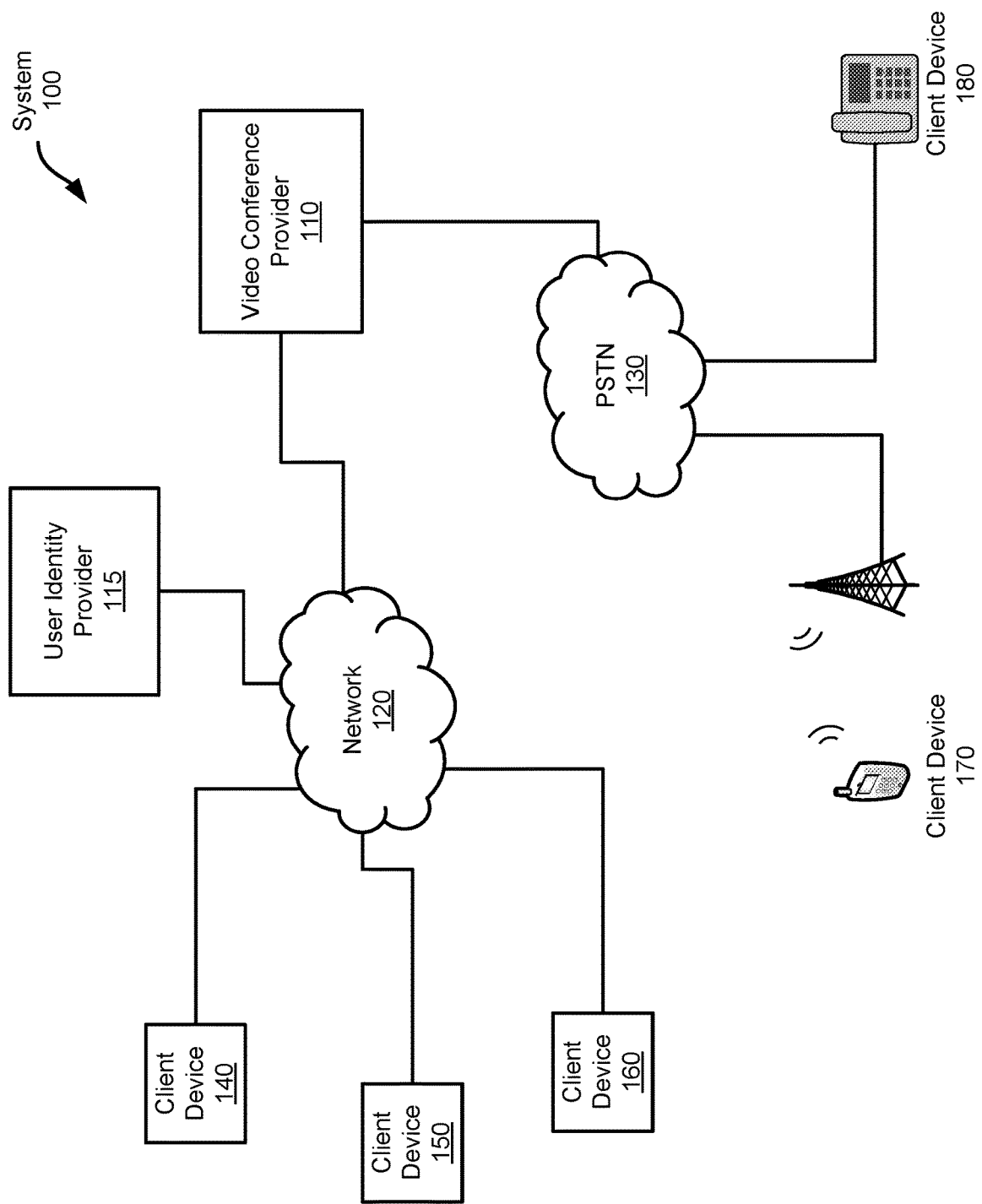
FIGS. 1-4 show example systems for providing dynamic content to video conference waiting rooms.

Examples are described herein in the context of systems and methods for providing dynamic content to video conference waiting rooms. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Video conferencing systems enable their users to create and attend video conferences (or "meetings") via various types of client devices. After joining a meeting, the participants receive audio and video streams or feeds (or "multimedia" streams or feeds) from the other participants and are presented with views of the video feeds from one or more of the other participants and audio from the audio feeds. When participating in video conference meetings, participants may view a graphical user interface ("GUI") provided by video conferencing software that provides various controls the participants can use to interact with the meeting or with other participants, and in which the video feeds of one or more participants may be seen. Such functionality allows the participants to see and hear each other, engage more deeply, and generally have a richer experience despite not being physically in the same space.

To create a meeting, a person (referred to as the "host" or "meeting host") accesses the video conferencing system, schedules a new meeting, and identifies one or more other people to invite to the meeting. In response to the host creating the meeting, the video conference system establishes the meeting by creating a meeting identifier and, if desired, a passcode or other access control information. The host can then send the meeting identifier (and access control information) to each of the invitees, such as by email. Once the meeting is started, the invitees can then access and join the meeting using the meeting identifier and any provided access control information.

When a participant attempts to join a video conference, the video conference provider may initially join them to a waiting room before allowing them to proceed into the main meeting itself. Waiting rooms may be provided in cases where the meeting host has not yet joined the meeting, the participant attempts to join the meeting before the scheduled start time, the meeting host desires to approve every participant's entry into the main meeting, etc.

While in a waiting room, the participant may be presented with an empty or otherwise static window (e.g. with text indicating that the user is in a waiting room) by the GUI indicating that the user is waiting to be admitted to the main video conference meeting. Once the user is admitted to the meeting, they will be able to view video feeds from other participants, but until then, they are simply presented with the static waiting room screen.

To provide a participant with more engaging or useful information while they are waiting to be admitted to a meeting, a video conference provider may provide dynamic content to the waiting room. For example, the video conference provider may provide pre-recorded videos, presentations, or interactive forms or tools for the participant to engage with. In addition, the dynamic content may be selected based on the type of meeting the user is attempting to join.

Video conference meetings may be used in a wide variety of contexts, but one example use may be a virtual doctor's appointment in a telehealth setting. A patient may schedule an appointment with their physician and set a date and time for the appointment. At the appointed time, the patient can contact the video conference provider to join the scheduled meeting. The video conference provider determines that the appointment is a doctor visit and obtains dynamic content that may be relevant to a patient about to have a checkup. The dynamic content may have been previously provided by the doctor's office, such as by uploading one or more videos suitable for its patients to view, or they may be selected from online content providers that may have data stores that include video content related to the annual doctor visits.

In this example, the video conference provider identifies available videos related to the doctor appointments, including information explaining typical tests run during such appointments, e.g., blood pressure testing and corresponding normal, low, or elevated blood pressures, information about body weight and BMI measurements, basic information about heart and lung tests that may be performed, etc. The video conference provider then determines an estimated wait time until the appointment is scheduled to begin and identifies, from the previously identified available, related videos, videos that have durations similar to the estimated wait time and selects a video with a high rating or one that was provided by the doctor's office itself.

Once the content has been selected, the video conference provider obtains the video and begins to play and stream the video and audio for the participant to view. In this example, the video conference provider has also received forms from the doctor's office that its patients fill out before their appointments, which may request updated insurance information, updated health information etc. If the patient is due to fill out a form, the video conference provider may, instead of selecting and playing a video, present questions from the form for the user to answer while in the waiting room. The user may be presented with dialog boxes having questions and options to select for answers. The video conference provider may obtain the answers and provide them to the doctor's office, which may facilitate the pre-appointment paperwork process.

Providing dynamic content to meeting participants who are first joined to waiting rooms may enable the participants to obtain helpful information prior to entering a main meeting or it may provide an opportunity for them to provide information or other content related to the meeting they intend to join. This may substantially improve the participant's experience both as they wait for their meeting to begin and to prepare them for the substance of that meeting.

This illustrative example is given to introduce the reader to the general subject matter discussed herein and the disclosure is not limited to this example. The following sections describe various additional non-limiting examples and examples of systems and methods for providing dynamic content to video conference waiting rooms.

Referring now to FIG. 1, FIG. 1 shows an example system 100 that provides videoconferencing functionality to various client devices. The system 100 includes a video conference provider 110 that is connected to multiple communication networks 120, 130, through which various client devices 140-180 can participate in video conferences hosted by the video conference provider 110. For example, the video conference provider 120 can be located within a private network to provide video conferencing services to devices within the private network, or it can be connected to a public network, e.g., the internet, so it may be accessed by anyone. Some examples may even provide a hybrid model in which a video conference provider 120 may supply components to enable a private organization to host private internal video conferences or to connect its system to the video conference provider 120 over a public network.

The system optionally also includes one or more user identity providers, e.g., user identity provider 115, which can provide user identity services to users of the client devices 140-160 and may authenticate user identities of one or more users to the video conference provider 110. In this example, the user identity provider 115 is operated by a different entity than the video conference provider 110, though in some examples, they may be the same entity.

Figure 2:
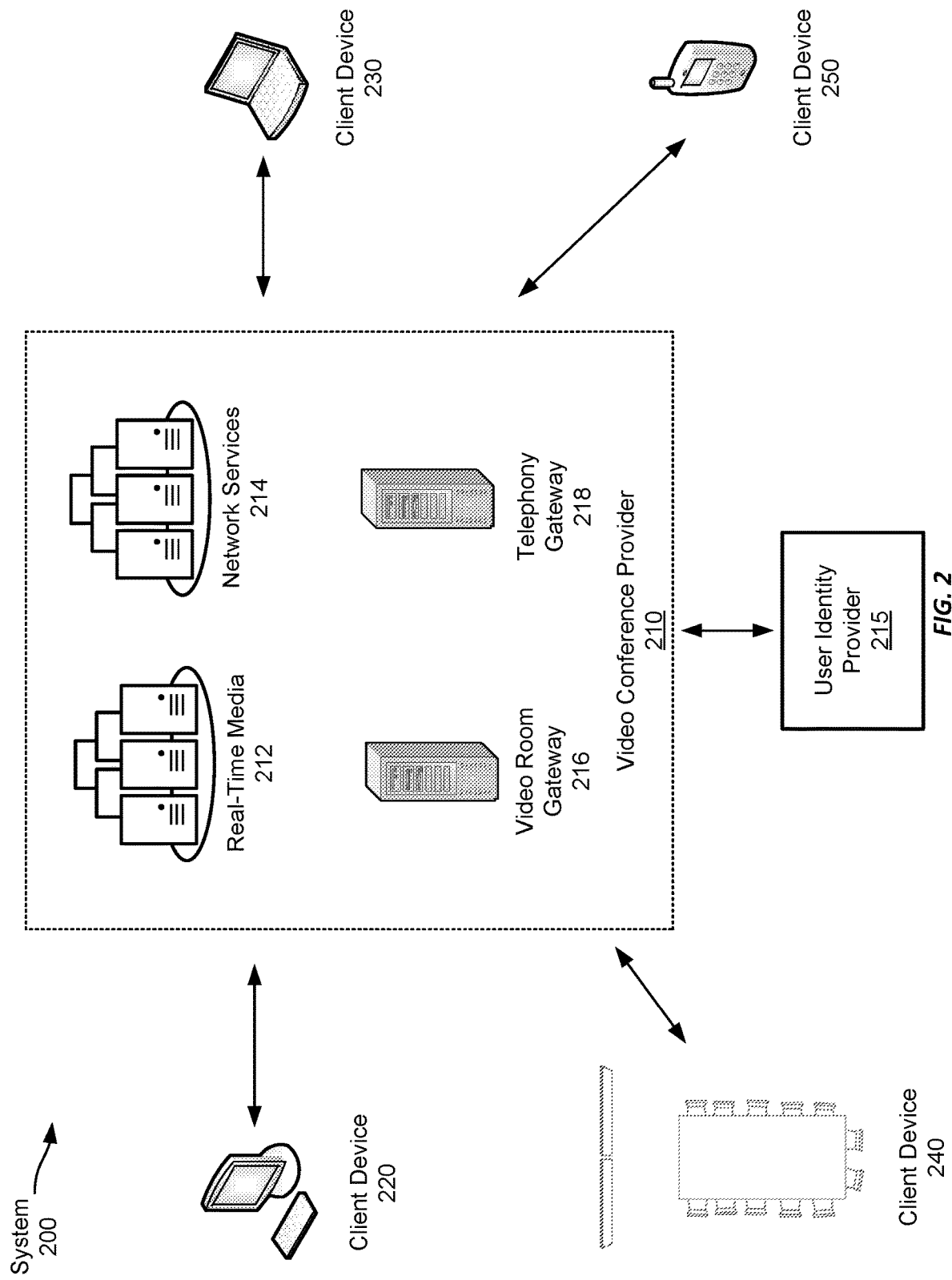

Video conference provider 110 allows clients to create video conference meetings (or "meetings") and invite others to participate in those meetings as well as perform other related functionality, such as recording the meetings, generating transcripts from meeting audio, manage user functionality in the meetings, enable text messaging during the meetings, create and manage breakout rooms from the main meeting, etc. FIG. 2, described below, provides a more detailed description of the architecture and functionality of the video conference provider 110.

Meetings in this example video conference provider 110 are provided in virtual "rooms" to which participants are connected. The room in this context is a construct provided by a server that provides a common point at which the various video and audio data is received before being multiplexed and provided to the various participants. While a "room" is the label for this concept in this disclosure, any suitable functionality that enables multiple participants to participate in a common video conference may be used. Further, in some examples, and as alluded to above, a meeting may also have "breakout" rooms. Such breakout rooms may also be rooms that are associated with a "main" video conference room. Thus, participants in the main video conference room may exit the room into a breakout room, e.g., to discuss a particular topic, before returning to the main room. The breakout rooms in this example are discrete meetings that are associated with the meeting in the main room. However, to join a breakout room, a participant must first enter the main room. A room may have any number of associated breakout rooms according to various examples.

To create a meeting with the video conference provider 110, a user may contact the video conference provider 110 using a client device 140-180 and select an option to create a new meeting. Such an option may be provided in a webpage accessed by a client device 140-160 or client application executed by a client device 140-160. For telephony devices, the user may be presented with an audio menu that they may navigate by pressing numeric buttons on their telephony device. To create the meeting, the video conference provider 110 may prompt the user for certain information, such as a date, time, and duration for the meeting, a number of participants, a type of encryption to use, whether the meeting is confidential or open to the public, etc. After receiving the various meeting settings, the video conference provider may create a record for the meeting and generate a meeting identifier and, in some examples, a corresponding meeting password or passcode (or other authentication information), all of which meeting information is provided to the meeting host.

After receiving the meeting information, the user may distribute the meeting information to one or more users to invite them to the meeting. To begin the meeting at the scheduled time (or immediately, if the meeting was set for an immediate start), the host provides the meeting identifier and, if applicable, corresponding authentication information (e.g., a password or passcode). The video conference system then initiates the meeting and may admit users to the meeting. Depending on the options set for the meeting, the users may be admitted immediately upon providing the appropriate meeting identifier (and authentication information, as appropriate), even if the host has not yet arrived, or the users may be presented with information indicating the that meeting has not yet started or the host may be required to specifically admit one or more of the users.

During the meeting, the participants may employ their client devices 140-180 to capture audio or video information and stream that information to the video conference provider 110. They also receive audio or video information from the video conference provider 210, which is displayed by the respective client device 140 to enable the various users to participate in the meeting.

At the end of the meeting, the host may select an option to terminate the meeting, or it may terminate automatically at a scheduled end time or after a predetermined duration. When the meeting terminates, the various participants are disconnected from the meeting and they will no longer receive audio or video streams for the meeting (and will stop transmitting audio or video streams). The video conference provider 110 may also invalidate the meeting information, such as the meeting identifier or password/passcode.

To provide such functionality, one or more client devices 140-180 may communicate with the video conference provider 110 using one or more communication networks, such as network 120 or the public switched telephone network ("PSTN") 130. The client devices 140-180 may be any suitable computing or communications device that have audio or video capability. For example, client devices 140-160 may be conventional computing devices, such as desktop or laptop computers having processors and computer-readable media, connected to the video conference provider 110 using the internet or other suitable computer network. Suitable networks include the internet, any local area network ("LAN"), metro area network ("MAN"), wide area network ("WAN"), cellular network (e.g., 3G, 4G, 4G LTE, 5G, etc.), or any combination of these. Other types of computing devices may be used instead or as well, such as tablets, smartphones, and dedicated video conferencing equipment. Each of these devices may provide both audio and video capabilities and may enable one or more users to participate in a video conference meeting hosted by the video conference provider 110.

In addition to the computing devices discussed above, client devices 140-180 may also include one or more telephony devices, such as cellular telephones (e.g., cellular telephone 170), internet protocol ("IP") phones (e.g., telephone 180), or conventional telephones. Such telephony devices may allow a user to make conventional telephone calls to other telephony devices using the PSTN, including the video conference provider 110. It should be appreciated that certain computing devices may also provide telephony functionality and may operate as telephony devices. For example, smartphones typically provide cellular telephone capabilities and thus may operate as telephony devices in the example system 100 shown in FIG. 1. In addition, conventional computing devices may execute software to enable telephony functionality, which may allow the user to make and receive phone calls, e.g., using a headset and microphone. Such software may communicate with a PSTN gateway to route the call from a computer network to the PSTN. Thus, telephony devices encompass any devices that can make conventional telephone calls and is not limited solely to dedicated telephony devices like conventional telephones.

Referring again to client devices 140-160, these devices 140-160 contact the video conference provider 110 using network 120 and may provide information to the video conference provider 110 to access functionality provided by the video conference provider 110, such as access to create new meetings or join existing meetings. To do so, the client devices 140-160 may provide user identification information, meeting identifiers, meeting passwords or passcodes, etc. In examples that employ a user identity provider 115, a client device, e.g., client devices 140-160, may operate in conjunction with a user identity provider 115 to provide user identification information or other user information to the video conference provider 110.

A user identity provider 115 may be any entity trusted by the video conference provider 110 that can help identify a user to the video conference provider 110. For example, a trusted entity may be a server operated by a business or other organization and with whom the user has established their identity, such as an employer or trusted third-party. The user may sign into the user identity provider 115, such as by providing a username and password, to access their identity at the user identity provider 115. The identity, in this sense, is information established and maintained at the user identity provider 115 that can be used to identify a particular user, irrespective of the client device they may be using. An example of an identity may be an email account established at the user identity provider 110 by the user and secured by a password or additional security features, such as biometric authentication, two-factor authentication, etc. However, identities may be distinct from functionality such as email. For example, a health care provider may establish identities for its patients. And while such identities may have associated email accounts, the identity is distinct from those email accounts. Thus, a user's "identity" relates to a secure, verified set of information that is tied to a particular user and should be accessible only by that user. By accessing the identity, the associated user may then verify themselves to other computing devices or services, such as the video conference provider 110.

When the user accesses the video conference provider 110 using a client device, the video conference provider 110 communicates with the user identity provider 115 using information provided by the user to verify the user's identity. For example, the user may provide a username or cryptographic signature associated with a user identity provider 115. The user identity provider 115 then either confirms the user's identity or denies the request. Based on this response, the video conference provider 110 either provides or denies access to its services, respectively.

For telephony devices, e.g., client devices 170-180, the user may place a telephone call to the video conference provider 110 to access video conference services. After the call is answered, the user may provide information regarding a video conference meeting, e.g., a meeting identifier ("ID"), a passcode or password, etc., to allow the telephony device to join the meeting and participate using audio devices of the telephony device, e.g., microphone(s) and speaker(s), even if video capabilities are not provided by the telephony device.

Because telephony devices typically have more limited functionality than conventional computing devices, they may be unable to provide certain information to the video conference provider 110. For example, telephony devices may be unable to provide user identification information to identify the telephony device or the user to the video conference provider 110. Thus, the video conference provider 110 may provide more limited functionality to such telephony devices. For example, the user may be permitted to join a meeting after providing meeting information, e.g., a meeting identifier and passcode, but they may be identified only as an anonymous participant in the meeting. This may restrict their ability to interact with the meetings in some examples, such as by limiting their ability to speak in the meeting, hear or view certain content shared during the meeting, or access other meeting functionality, such as joining breakout rooms or engaging in text chat with other participants in the meeting.

It should be appreciated that users may choose to participate in meetings anonymously and decline to provide user identification information to the video conference provider 110, even in cases where the user has an authenticated identity and employs a client device capable of identifying the user to the video conference provider 110. The video conference provider 110 may determine whether to allow such anonymous users to use services provided by the video conference provider 110. Anonymous users, regardless of the reason for anonymity, may be restricted as discussed above with respect to users employing telephony devices, and in some cases may be prevented from accessing certain meetings or other services, or may be entirely prevented from accessing the video conference provider 110.

Referring again to video conference provider 110, in some examples, it may allow client devices 140-160 to encrypt their respective video and audio streams to help improve privacy in their meetings. Encryption may be provided between the client devices 140-160 and the video conference provider 110 or it may be provided in an end-to-end configuration where multimedia streams transmitted by the client devices 140-160 are not decrypted until they are received by another client device 140-160 participating in the meeting. Encryption may also be provided during only a portion of a communication, for example encryption may be used for otherwise unencrypted communications that cross international borders.

Client-to-server encryption may be used to secure the communications between the client devices 140-160 and the video conference provider 110, while allowing the video conference provider 110 to access the decrypted multimedia streams to perform certain processing, such as recording the meeting for the participants or generating transcripts of the meeting for the participants. End-to-end encryption may be used to keep the meeting entirely private to the participants without any worry about a video conference provider 110 having access to the substance of the meeting. Any suitable encryption methodology may be employed, including key-pair encryption of the streams. For example, to provide end-to-end encryption, the meeting host's client device may obtain public keys for each of the other client devices participating in the meeting and securely exchange a set of keys to encrypt and decrypt multimedia content transmitted during the meeting. Thus the client devices 140-160 may securely communicate with each other during the meeting. Further, in some examples, certain types of encryption may be limited by the types of devices participating in the meeting. For example, telephony devices may lack the ability to encrypt and decrypt multimedia streams. Thus, while encrypting the multimedia streams may be desirable in many instances, it is not required as it may prevent some users from participating in a meeting.

By using the example system shown in FIG. 1, users can create and participate in meetings using their respective client devices 140-180 via the video conference provider 110. Further, such a system enables users to use a wide variety of different client devices 140-180 from traditional standards-based video conferencing hardware to dedicated video conferencing equipment to laptop or desktop computers to handheld devices to legacy telephony devices, etc.

Referring now to FIG. 2, FIG. 2 shows an example system 200 in which a video conference provider 210 provides videoconferencing functionality to various client devices 220-250. The client devices 220-250 include two conventional computing devices 220-230, dedicated equipment for a video conference room 240, and a telephony device 250. Each client device 220-250 communicates with the video conference provider 210 over a communications network, such as the internet for client devices 220-240 or the PSTN for client device 250, generally as described above with respect to FIG. 1. The video conference provider 210 is also in communication with one or more user identity providers 215, which can authenticate various users to the video conference provider 210 generally as described above with respect to FIG. 1.

In this example, the video conference provider 210 employs multiple different servers (or groups of servers) to provide different aspects of video conference functionality, thereby enabling the various client devices to create and participate in video conference meetings. The video conference provider 210 uses one or more real-time media servers 212, one or more network services servers 214, one or more video room gateways 216, and one or more telephony gateways 218. Each of these servers 212-218 is connected to one or more communications networks to enable them to collectively provide access to and participation in one or more video conference meetings to the client devices 220-250.

The real-time media servers 212 provide multiplexed multimedia streams to meeting participants, such as the client devices 220-250 shown in FIG. 2. While video and audio streams typically originate at the respective client devices, they are transmitted from the client devices 220-250 to the video conference provider 210 via one or more networks where they are received by the real-time media servers 212. The real-time media servers 212 determine which protocol is optimal based on, for example, proxy settings and the presence of firewalls, etc. For example, the client device might select among UDP, TCP, TLS, or HTTPS for audio and video and UDP for content screen sharing.

The real-time media servers 212 then multiplex the various video and audio streams based on the target client device and communicate multiplexed streams to each client device. For example, the real-time media servers 212 receive audio and video streams from client devices 220-240 and only an audio stream from client device 250. The real-time media servers 212 then multiplex the streams received from devices 230-250 and provide the multiplexed streams to client device 220. The real-time media servers 212 are adaptive, for example, reacting to real-time network and client changes, in how they provide these streams. For example, the real-time media servers 212 may monitor parameters such as a client's bandwidth CPU usage, memory and network I/O as well as network parameters such as packet loss, latency and jitter to determine how to modify the way in which streams are provided.

The client device 220 receives the stream, performs any decryption, decoding, and demultiplexing on the received streams, and then outputs the audio and video using the client device's video and audio devices. In this example, the real-time media servers do not multiplex client device 220's own video and audio feeds when transmitting streams to it. Instead each client device 220-250 only receives multimedia streams from other client devices 220-250. For telephony devices that lack video capabilities, e.g., client device 250, the real-time media servers 212 only deliver multiplex audio streams. The client device 220 may receive multiple streams for a particular communication, allowing the client device 220 to switch between streams to provide a higher quality of service.

In addition to multiplexing multimedia streams, the real-time media servers 212 may also decrypt incoming multimedia stream in some examples. As discussed above, multimedia streams may be encrypted between the client devices 220-250 and the video conference system 210. In some such examples, the real-time media servers 212 may decrypt incoming multimedia streams, multiplex the multimedia streams appropriately for the various clients, and encrypt the multiplexed streams for transmission.

In some examples, to provide multiplexed streams, the video conference provider 210 may receive multimedia streams from the various participants and publish those streams to the various participants to subscribe to and receive. Thus, the video conference provider 210 notifies a client device, e.g., client device 220, about various multimedia streams available from the other client devices 230-250, and the client device 220 can select which multimedia stream(s) to subscribe to and receive. In some examples, the video conference provider 210 may provide to each client device the available streams from the other client devices, but from the respective client device itself, though in other examples it may provide all available streams to all available client devices. Using such a multiplexing technique, the video conference provider 210 may enable multiple different streams of varying quality, thereby allowing client devices to change streams in real-time as needed, e.g., based on network bandwidth, latency, etc.

As mentioned above with respect to FIG. 1, the video conference provider 210 may provide certain functionality with respect to unencrypted multimedia streams at a user's request. For example, the meeting host may be able to request that the meeting be recorded or that a transcript of the audio streams be prepared, which may then be performed by the real-time media servers 212 using the decrypted multimedia streams, or the recording or transcription functionality may be off-loaded to a dedicated server (or servers), e.g., cloud recording servers, for recording the audio and video streams. In some examples, the video conference provider 210 may allow a meeting participant to notify it of inappropriate behavior or content in a meeting. Such a notification may trigger the real-time media servers to 212 record a portion of the meeting for review by the video conference provider 210. Still other functionality may be implemented to take actions based on the decrypted multimedia streams at the video conference provider, such as monitoring video or audio quality, adjusting or changing media encoding mechanisms, etc.

It should be appreciated that multiple real-time media servers 212 may be involved in communicating data for a single meeting and multimedia streams may be routed through multiple different real-time media servers 212. In addition, the various real-time media servers 212 may not be co-located, but instead may be located at multiple different geographic locations, which may enable high-quality communications between clients that are dispersed over wide geographic areas, such as being located in different countries or on different continents. Further, in some examples, one or more of these servers may be co-located on a client's premises, e.g., at a business or other organization. For example, different geographic regions may each have one or more real-time media servers 212 to enable client devices in the same geographic region to have a high-quality connection into the video conference provider 210 via local servers 212 to send and receive multimedia streams, rather than connecting to a real-time media server located in a different country or on a different continent. The local real-time media servers 212 may then communicate with physically distant servers using high-speed network infrastructure, e.g., internet backbone network(s), that otherwise might not be directly available to client devices 220-250 themselves. Thus, routing multimedia streams may be distributed throughout the video conference system 210 and across many different real-time media servers 212.

Turning to the network services servers 214, these servers 214 provide administrative functionality to enable client devices to create or participate in meetings, send meeting invitations, create or manage user accounts or subscriptions, and other related functionality. Further, these servers may be configured to perform different functionalities or to operate at different levels of a hierarchy, e.g., for specific regions or localities, to manage portions of the video conference provider under a supervisory set of servers. When a client device 220-250 accesses the video conference provider 210, it will typically communicate with one or more network services servers 214 to access their account or to participate in a meeting.

When a client device 220-250 first contacts the video conference provider 210 in this example, it is routed to a network services server 214. The client device may then provide access credentials for a user, e.g., a username and password or single sign-on credentials, to gain authenticated access to the video conference provider 210. This process may involve the network services servers 214 contacting a user identity provider 215 to verify the provided credentials. Once the user's credentials have been accepted, the client device 214 may perform administrative functionality, like updating user account information, if the user has an identity with the video conference provider 210, or scheduling a new meeting, by interacting with the network services servers 214.

In some examples, users may access the video conference provider 210 anonymously. When communicating anonymously, a client device 220-250 may communicate with one or more network services servers 214 but only provide information to create or join a meeting, depending on what features the video conference provider allows for anonymous users. For example, an anonymous user may access the video conference provider using client 220 and provide a meeting ID and passcode. The network services server 214 may use the meeting ID to identify an upcoming or on-going meeting and verify the passcode is correct for the meeting ID. After doing so, the network services server(s) 214 may then communicate information to the client device 220 to enable the client device 220 to join the meeting and communicate with appropriate real-time media servers 212.

In cases where a user wishes to schedule a meeting, the user (anonymous or authenticated) may select an option to schedule a new meeting and may then select various meeting options, such as the date and time for the meeting, the duration for the meeting, a type of encryption to be used, one or more users to invite, privacy controls (e.g., not allowing anonymous users, preventing screen sharing, manually authorize admission to the meeting, etc.), meeting recording options, etc. The network services servers 214 may then create and store a meeting record for the scheduled meeting. When the scheduled meeting time arrives (or within a threshold period of time in advance), the network services server(s) 214 may accept requests to join the meeting from various users.

To handle requests to join a meeting, the network services server(s) 214 may receive meeting information, such as a meeting ID and passcode, from one or more client devices 220-250. The network services server(s) 214 locate a meeting record corresponding to the provided meeting ID and then confirm whether the scheduled start time for the meeting has arrived, whether the meeting host has started the meeting, and whether the passcode matches the passcode in the meeting record. If the request is made by the host, the network services server(s) 214 activates the meeting and connects the host to a real-time media server 212 to enable the host to begin sending and receiving multimedia streams.

Once the host has started the meeting, subsequent users requesting access will be admitted to the meeting if the meeting record is located and the passcode matches the passcode supplied by the requesting client device 220-250. In some examples additional access controls may be used as well. But if the network services server(s) 214 determines to admit the requesting client device 220-250 to the meeting, the network services server 214 identifies a real-time media server 212 to handle multimedia streams to and from the requesting client device 220-250 and provides information to the client device 220-250 to connect to the identified real-time media server 212. Additional client devices 220-250 may be added to the meeting as they request access through the network services server(s) 214.

After joining a meeting, client devices will send and receive multimedia streams via the real-time media servers 212, but they may also communicate with the network services servers 214 as needed during meetings. For example, if the meeting host leaves the meeting, the network services server(s) 214 may appoint another user as the new meeting host and assign host administrative privileges to that user. Hosts may have administrative privileges to allow them to manage their meetings, such as by enabling or disabling screen sharing, muting or removing users from the meeting, creating sub-meetings or "break-out" rooms, recording meetings, etc. Such functionality may be managed by the network services server(s) 214.

For example, if a host wishes to remove a user from a meeting, they may identify the user and issue a command through a user interface on their client device. The command may be sent to a network services server 214, which may then disconnect the identified user from the corresponding real-time media server 212. If the host wishes to create a break-out room for one or more meeting participants to join, such a command may also be handled by a network services server 214, which may create a new meeting record corresponding to the break-out room and then connect one or more meeting participants to the break-out room similarly to how it originally admitted the participants to the meeting itself.

In addition to creating and administering on-going meetings, the network services server(s) 214 may also be responsible for closing and tearing-down meetings once they have completed. For example, the meeting host may issue a command to end an on-going meeting, which is sent to a network services server 214. The network services server 214 may then remove any remaining participants from the meeting, communicate with one or more real time media servers 212 to stop streaming audio and video for the meeting, and deactivate, e.g., by deleting a corresponding passcode for the meeting from the meeting record, or delete the meeting record(s) corresponding to the meeting. Thus, if a user later attempts to access the meeting, the network services server(s) 214 may deny the request.

Depending on the functionality provided by the video conference provider, the network services server(s) 214 may provide additional functionality, such as by providing private meeting capabilities for organizations, special types of meetings (e.g., webinars), etc. Such functionality may be provided according to various examples of video conferencing providers according to this description.

Referring now to the video room gateway servers 216, these servers 216 provide an interface between dedicated video conferencing hardware, such as may be used in dedicated video conferencing rooms. Such video conferencing hardware may include one or more cameras and microphones and a computing device designed to receive video and audio streams from each of the cameras and microphones and connect with the video conference provider 210. For example, the video conferencing hardware may be provided by the video conference provider to one or more of its subscribers, which may provide access credentials to the video conferencing hardware to use to connect to the video conference provider 210.

The video room gateway servers 216 provide specialized authentication and communication with the dedicated video conferencing hardware that may not be available to other client devices 220-230, 250. For example, the video conferencing hardware may register with the video conference provider 210 when it is first installed and the video room gateway servers 216 may authenticate the video conferencing hardware using such registration as well as information provided to the video room gateway server(s) 216 when dedicated video conferencing hardware connects to it, such as device ID information, subscriber information, hardware capabilities, hardware version information etc. Upon receiving such information and authenticating the dedicated video conferencing hardware, the video room gateway server(s) 216 may interact with the network services servers 214 and real-time media servers 212 to allow the video conferencing hardware to create or join meetings hosted by the video conference provider 210.

Referring now to the telephony gateway servers 218, these servers 218 enable and facilitate telephony devices' participation in meetings hosed by the video conference provider 210. Because telephony devices communicate using the PSTN and not using computer networking protocols, such as TCP/IP, the telephony gateway servers 218 act as an interface that converts between the PSTN and the networking system used by the video conference provider 210.

For example, if a user uses a telephony device to connect to a meeting, they may dial a phone number corresponding to one of the video conference provider's telephony gateway servers 218. The telephony gateway server 218 will answer the call and generate audio messages requesting information from the user, such as a meeting ID and passcode. The user may enter such information using buttons on the telephony device, e.g., by sending dual-tone multi-frequency ("DTMF") audio signals to the telephony gateway server 218. The telephony gateway server 218 determines the numbers or letters entered by the user and provides the meeting ID and passcode information to the network services servers 214, along with a request to join or start the meeting, generally as described above. Once the telephony client device 250 has been accepted into a meeting, the telephony gateway server 218 is instead joined to the meeting on the telephony device's behalf.

After joining the meeting, the telephony gateway server 218 receives an audio stream from the telephony device and provides it to the corresponding real-time media server 212, and receives audio streams from the real-time media server 212, decodes them, and provides the decoded audio to the telephony device. Thus, the telephony gateway servers 218 operate essentially as client devices, while the telephony device operates largely as an input/output device, e.g., a microphone and speaker, for the corresponding telephony gateway server 218, thereby enabling the user of the telephony device to participate in the meeting despite not using a computing device or video.

It should be appreciated that the components of the video conference provider 210 discussed above are merely examples of such devices and an example architecture. Some video conference providers may provide more or less functionality than described above and may not separate functionality into different types of servers as discussed above. Instead, any suitable servers and network architectures may be used according to different examples.

Figure 3:
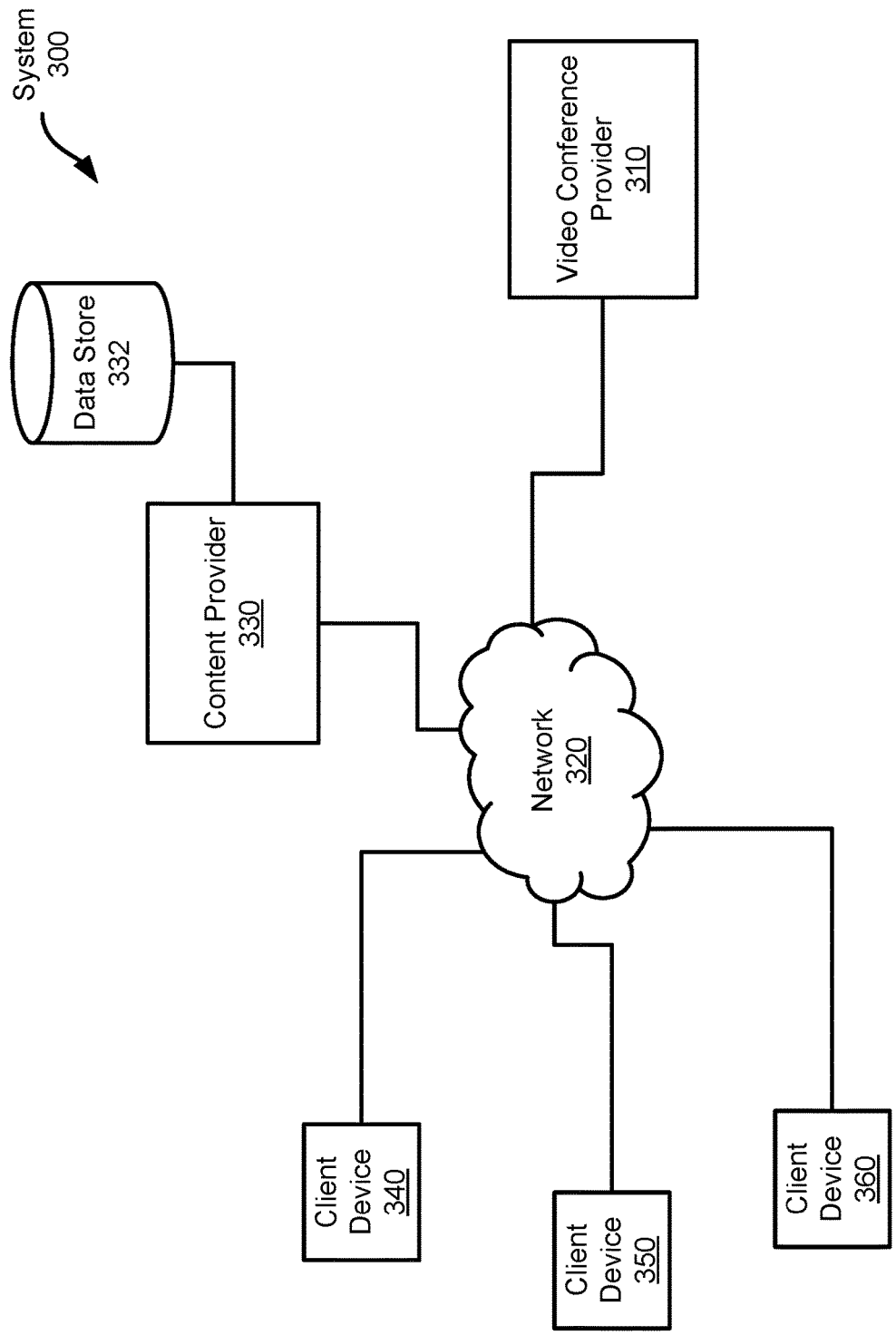

Referring now to FIG. 3, FIG. 3 shows an example system 300 for providing dynamic content to video conference waiting rooms. The example system 300 includes a video conference provider 310 that provides video conference services via network 320, e.g., the internet, generally as described above with respect to FIGS. 1-2. Multiple client devices 340-360 are also connected to the network and are able to schedule, create, join, and participate in video conference meetings hosted by the video conference provider 310, also as provided above. In addition, a content provider 330 and its associated data store 332 is connected to the network and may communicate with the video conference provider and the client devices 340-360.

As discussed above with respect to FIGS. 1-2, the video conference provider 310 is able to host meetings to allow the meeting participants to engage with each other through video and audio feeds exchanged among the participants and facilitated by the video conference provider 310. However, in some examples, a meeting host may select an option to require participants to enter a waiting room before joining the meeting. To provide this functionality, the video conference provider 310 connects the new participant to the main meeting; however it does not provide cryptographic keys to the new participant's client device 340a. Thus, while the client device 340a could retrieve multimedia streams available in the main meeting, they could not be decrypted. In this example, video conference software executed by the client device 340a determines that it has not received cryptographic keys and thus does not attempt to obtain any multimedia streams and does not provide multimedia streams to the video conference provider 310. Thus, the participant is kept in a waiting state with respect to the main meeting, and thus is in a "waiting" room. Further, because the participant is connected to the main meeting, additional participants that also attempt to connect to the main meeting would similarly be kept in the waiting room. At a later time, the client device 340a may be admitted to the main meeting and the video conference provider 310 may supply cryptographic keys to the client device 340a to enable it to encrypt or decrypt multimedia streams, thereby enabling the participant to participate in the main meeting.

In some examples, rather than connect participant client devices to the main meeting, but not providing cryptographic keys, the video conference provider 310 can establish separate "anonymous" meetings associated with the main meeting scheduled by the host to serve as waiting rooms for participants seeking to enter the main meeting. These waiting rooms are anonymous in the sense that they do not have access information generally available to be discovered and joined. Instead, they are created as needed and information to join the waiting room is supplied to a participant's client device, but is not otherwise made available for others to join. In addition, the waiting rooms are not created as interactive meetings. Thus, while in this example, each participant is assigned to their own waiting room, in examples that allow multiple participants to all be joined to the same waiting room, the participants would not send multimedia feeds to the video conference provider 310, and the video conference provider 310 does not distribute information about any other participants in the waiting room to any participant in the waiting room.

When a participant, via their client device 340-360, request to join a main meeting of a video conference, but is instead joined to a waiting room by the video conference provider 310, the video conference provider 310 may identify content to present to the participant while they are in the waiting room. For example, a participant using client device 340 may attempt to join a meeting hosted by an online educational institution.

An instructor from the educational institution, using client device 360, may schedule meetings with the video conference provider 310 for classes in a course of study that the instructor will be teaching over a period of time. When scheduling the classes, the instructor may provide information about the subject of each class to the video conference provider 310, such as by providing a title for the class or a brief description of the class that may be distributed to the participants within invitations to the classes. In addition to scheduling the classes, the instructor may also provide content items to the video conference provider that may be presented to participants before they join the classes. For example, the instructor may provide presentations or videos associated with various classes during the course of study, such as video summaries of the classes, worksheets for the classes, surveys or questionnaires, etc. At a later time, when a participant joins the meeting and is instead routed to a waiting room, the content provider may access the content items provided by the instructor (via client device 360) and select one or more of the content items to present to a participant that is joined to a waiting room.

To select a content item, the video conference provider 310 may access information about the class, such as a title of the class or a brief description as described above. In addition, information about the host or the participant may be available to the video conference provider 310. For example, the host or the participant may have an account with the video conference provider 310 that includes information about their title or position, their department, their employer, etc. Similarly, the host may maintain a contact list available to the video conference provider 310 that identifies information about the participant, such as whether the participant is a client or customer, a vendor, a candidate for a position, etc. The video conference provider may access such information to select suitable content.

Based on the information about the class, the host, or the participants, the video conference provider may identify a content item that may be accessed and presented to the participant. For example, the video conference provider may identify a video based on a filename of the file or metadata within the video identifying the subject matter of the video. The instructor may name the files based on their content, e.g., "Class 7—Review of Major Topics." Thus, when a participant attempts to join a scheduled class, the video conference provider 310 accesses information about the class, e.g., the title ("Class 8—Robotic Computer Vision"), and identify the class number (8). It may use such information to identify content items related to class 8, e.g., a short introduction video intended to introduce the students to the major topics to be covered by the class, or to prior classes, such as the review video for class 7.

In another example, if the host is in a purchasing role for a company and the participant is a vendor, the video conference provider 310 may select a video item from available videos related to the vendor relationship, such as recent changes to invoicing procedures. Alternatively, the host may be an employee who has invited an HR professional to a videoconference to discuss a review. The video conference provider may identify a keyword in the meeting title, e.g., "review," the title for the employee, and the title for the HR professional, and identify content related to the meeting, such as an annual review form completed for the employee by the employer.

Upon identifying one or more content items, the video conference provider 310 may select one to present, e.g., the Class 7 review video. After the participant has joined the waiting room, it may create video and audio streams for the participant's client device 340 to subscribe to and begin playback of the video. Alternatively, the video conference provider 310 may identify a brief quiz related to the prior class, and present the participant with a series of dialog boxes with questions and multiple options for responses to each. The video conference provider 310 may receive the responses and compile them for the participant, and ultimately provide them to the instructor for review.

In some examples, however, rather than a meeting host providing content items, the video conference provider 310 may communicate with the content provider 330 to identify potentially relevant content items for a scheduled meeting. For example, if a participant requests to join a meeting that has been scheduled as a doctor's appointment for a health checkup and with a brief description identifying potential tests or procedures during the appointment, the video conference provider may issue search queries to the content provider 330 based on one or more keywords or concepts in the title of the meeting or within the brief description. The video conference provider 310 may employ a pre-defined list of keywords or natural language processing ("NLP") to identify keywords or concepts and then create search queries using such information.

In response to the search queries, the content provider 330 accesses its data store 332 to search for relevant content items, such as videos. The search results may be provided to the video conference provider 310, which may then attempt to identify videos to present, such as based on a number of views for each video or viewer ratings of the videos. Once a suitable video has been identified, it may be played to the participant in the waiting room by publishing audio and video feeds for the participant's client device 340 to subscribe to and present to the participant.

While the examples above have been in the medical or educational context, other examples may be applicable in other contexts, including corporate, governmental, non-profit, etc.

Figure 4:
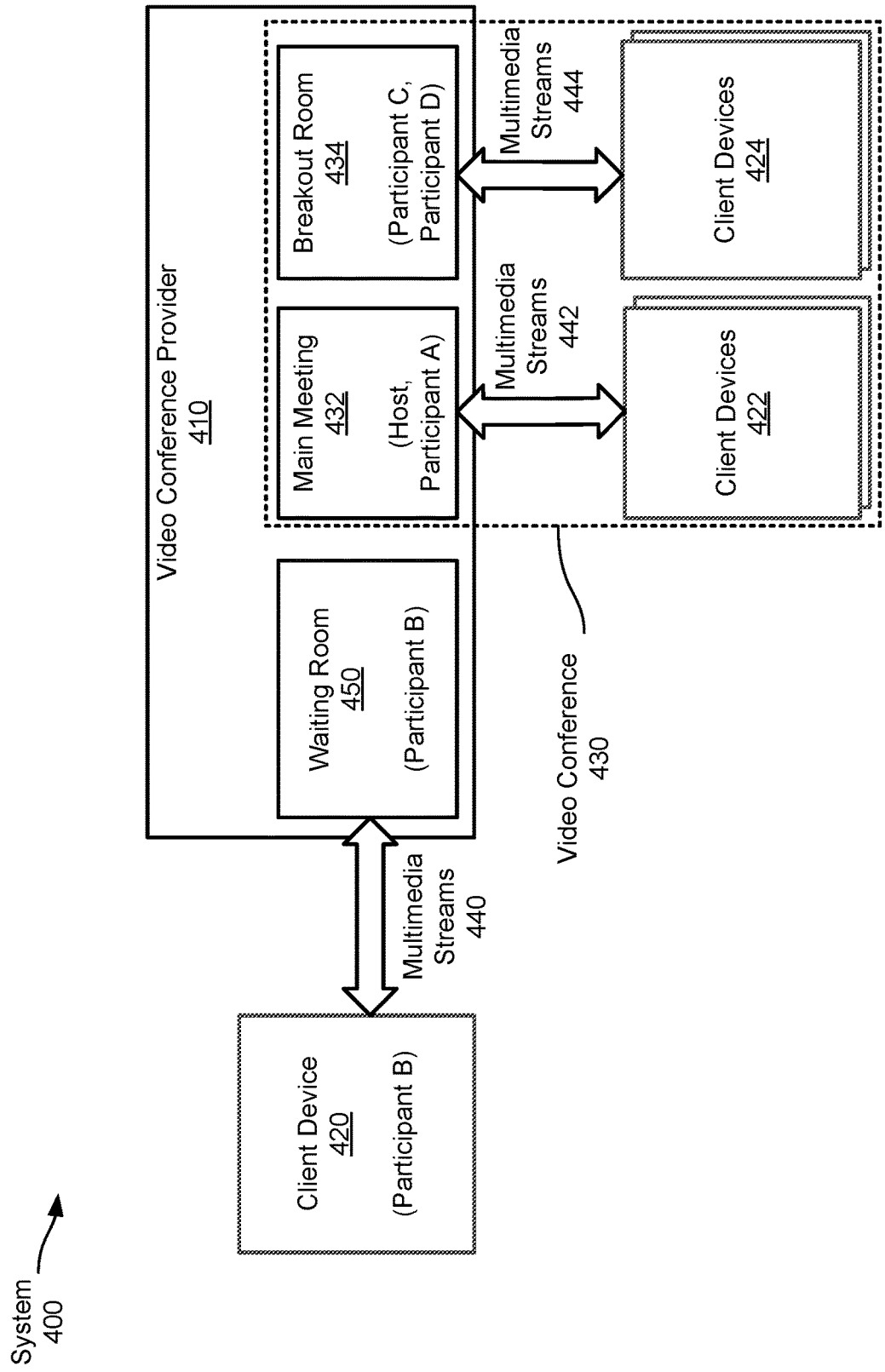

Referring now to FIG. 4, FIG. 4 shows an example system 400 for providing dynamic content to video conference waiting rooms. In this example, the system 400 includes video conference provider 410, generally as discussed above with respect to FIGS. 1-3. The system 400 shows more detail of different functionality provided by the video conference provider 410 to enable providing waiting rooms in conjunction with other video conferences. The video conference provider 410 can create a video conference 430 that includes a main meeting 432 to which various participants can join. The main meeting 432 then becomes the virtual nexus through which the participant client devices 422 connect and exchange multimedia streams 442 to interact with each other. The video conference provider 410 may also enable video conferences 430 to employ breakout rooms 434 from main meetings 432 to allow subsets of participants (e.g. participants C and D) in the main meeting to exit the main meeting and join the breakout room, via their client devices 424, to discuss any topics of relevance, but without leaving the video conference 430.

When a new participant, e.g., participant B, uses their client device 420 to attempt to join the video conference 430, the video conference provider 410 receives the request and determines that the video conference 430 has been configured to require new participants to be placed into a waiting room 450 before they will be admitted to the video conference 430. However, because there is no participant interaction in a waiting room, the video conference provider does not provide cryptographic keys that would allow the participant to encrypt or decrypt multimedia streams to exchange with other participants. Thus, in this example, the video conference provider 410 joins the client device 420 to the main meeting, but does not provide cryptographic keys needed to decrypt incoming multimedia streams or to encrypt outgoing multimedia streams. In another example the video conference provider 410 creates a waiting room 450 (if one does not already exist, e.g., the main meeting has not been established yet or separate waiting rooms are employed) and joins the participant's client device 420 to the waiting room. In some examples, video conference software executed by the client device 420 determines that no cryptographic keys have been received and thus, the video conference software will not attempt to access to any multimedia streams to receive and will not attempt to generate any multimedia streams to transmit.

The video conference provider 410 then determines whether any dynamic content should be provided to the new participant. For example, the video conference may have been configured to indicate that dynamic content should be provided to participants in a waiting room. The meeting host may make such a selection when scheduling the meeting, or the selection may be automatically enabled by the video conference provider, unless the meeting host elects to disable the option.

If dynamic content is to be provided to the participant, the video conference provider 410 identifies suitable dynamic content and presents it to the client device via one or more multimedia streams 440. In some cases, the dynamic content may not be interactive, such as for a video playback, though in other examples, the participant may provide one or more multimedia streams to the waiting room, e.g., to provide responses to questions posed to the participant.

At some time after the client device 420 has joined the waiting room 450, the video conference provider 410 joins the client device 420 to the main meeting 432. This may occur based on the host of the video conference selecting an option to admit the participant to the main meeting. In another example, the video conference provider 410 may automatically join the client device 420 to the main meeting 432 once the dynamic content has concluded, e.g., the selected video has ended or the participant has answered any questions presented to them.

While the example system 400 in FIG. 4 only illustrates an example with a single waiting room 450, it should be appreciated that the video conference provider 410 may support any number of video conferences and any number of waiting rooms, generally as described above. Further, in some examples, the video conference provider 410 may be configured to create a new waiting room for each new participant so that each participant is in a different waiting room, or in some examples, the video conference provider 410 may join multiple different participants to the same waiting room.

Figure 5:
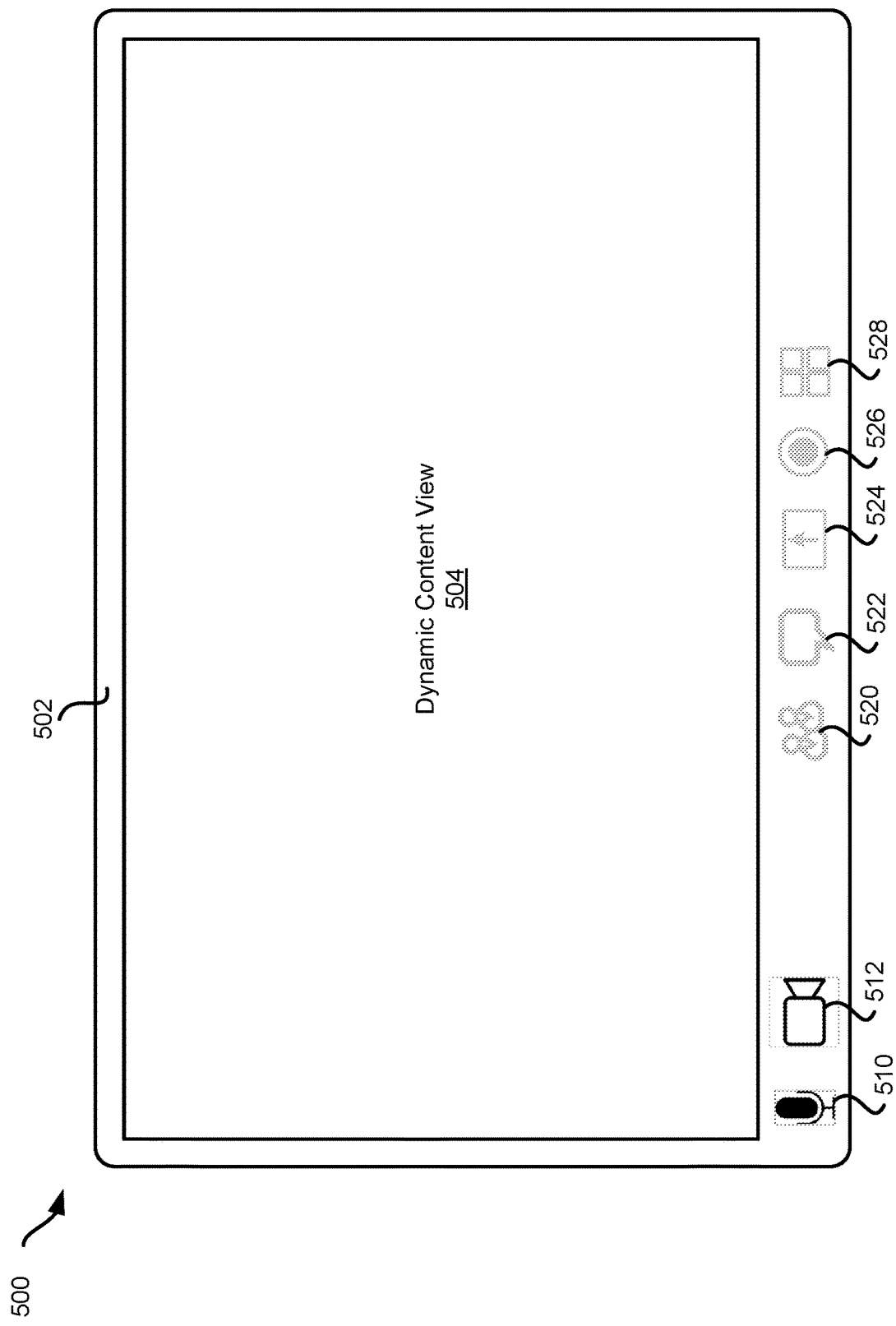
FIGS. 5-6 show example graphical user interfaces suitable for use with various systems and methods for providing dynamic content to video conference waiting rooms.

Referring now to FIG. 5, FIG. 5 shows an example GUI 500 that may be provided to a participant by video conferencing software executed by their client device. In this example, the GUI 500 includes a dynamic content view 504 in the center of the GUI 500. The dynamic content view 502 is surrounded by a border 502, which includes a number of interactive elements 510-528 to allow the participant to interact with the video conference software. Controls 510-512 may allow the user to toggle on or off audio or video streams captured by a microphone or camera connected to the client device. Control 520 allows the participant to view any other participants in the meeting with the participant, while control 522 allows the user to send text messages to other participants, whether to specific participants or to the entire meeting. Control 524 allows the participant to share content from their client device. Control 526 allows the participant toggle recording of the meeting, and control 528 allows the user to select an option to join a breakout room. In this example, each of these options is disabled because waiting rooms provided by the video conference provider do not support such functionality, though other meeting rooms do.

Upon entering a waiting room, video conference software executed by the participant's client device may present a GUI, such as GUI 500, to the participant to enable them to view dynamic content presented in the waiting room. As discussed above, the video conference provider may select dynamic content to provide to the participant and provide one or more multimedia streams to the client device. The dynamic content may then be displayed in the dynamic content area 504, such as by displaying video or by presenting questions or other interactive content. It should be appreciated that the dynamic content area 504 may also include additional GUI elements that may be displayed to the user as a part of the dynamic content.

Figure 6:
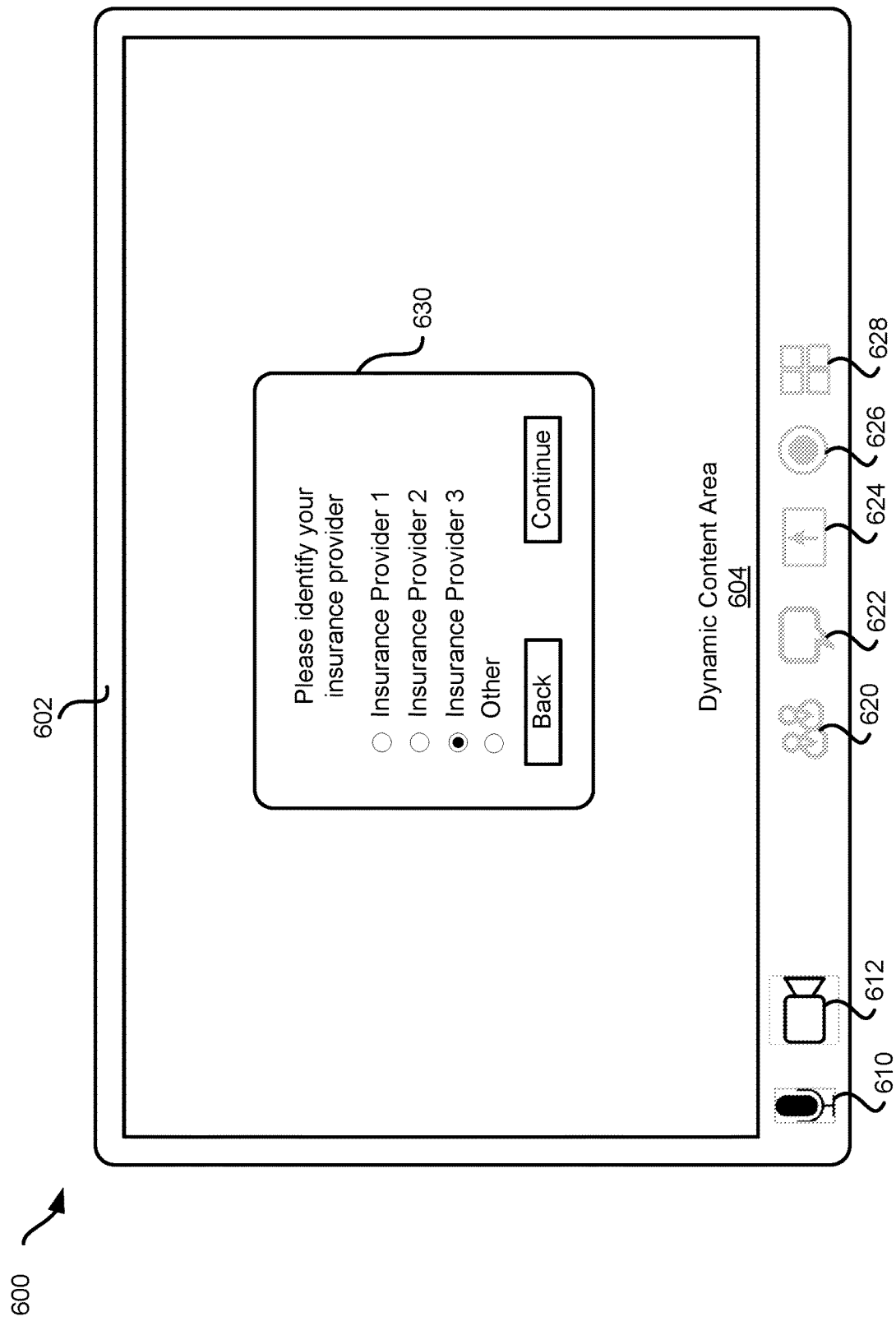

For example, referring to FIG. 6, which shows another example GUI 600, the GUI 600 includes the same controls 610-628 and a dynamic content area 604 similar to the example shown in FIG. 5. In this example, the video conference provider has provided a questionnaire (or form) to the participant in the waiting room that includes various questions relating to a medical appointment. Questions in the questionnaire are presented in one or more dialog boxes 630 as selectable options, in this case to identify the participant's insurance provider. While this example provides a list of selectable options, other examples may allow the user to select options from other types of GUI elements, e.g., drop-down boxes. Some examples may also allow the participant to type information into a field, such as to provide free-form text answers, etc. After receiving responses to the various questions on the questionnaire, the video conference provider may provide them to the meeting host when the participant is admitted into the main meeting of video conference. Such information may be provided as a downloadable document, in an interactive window in the host's video conference software's GUI, or any other suitable form.

Figure 7:
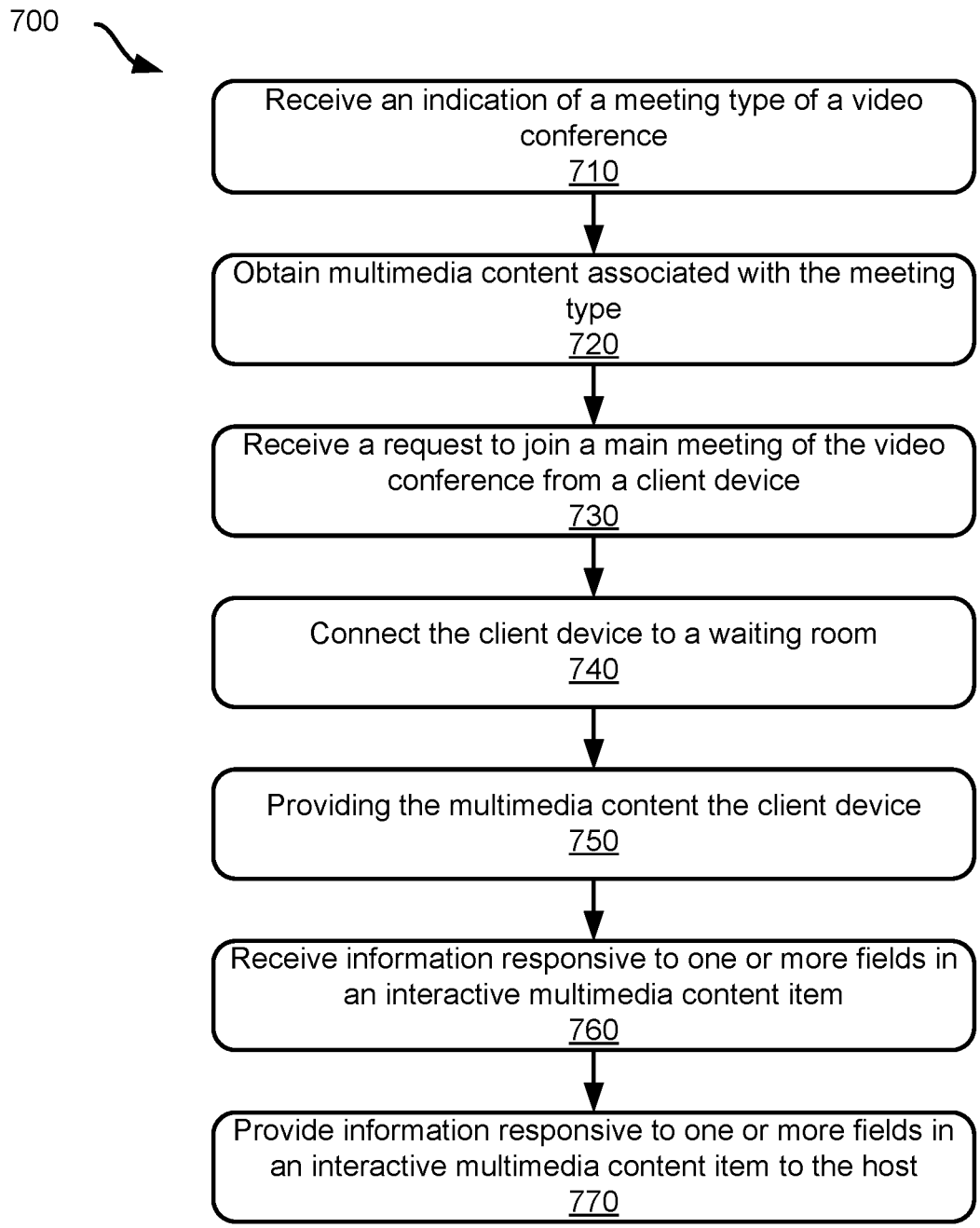
FIG. 7 shows an example method for providing dynamic content to video conference waiting rooms.

Referring now to FIG. 7, FIG. 7 shows an example method 700 for providing dynamic content to video conference waiting rooms. The method 700 will be described with respect to the system 300 shown in FIG. 3; however, methods according to this disclosure may employ any suitable systems according to this disclosure, such as the systems 100, 200, 400 shown in FIGS. 1-2 and 4.

At block 710, the video conference provider 310 receives an indication of a meeting type of a video conference. As discussed above, when a meeting host schedules a meeting, the host may include information describing the nature of the meeting, such as in the title of the meeting, in a brief description of the meeting, or in an agenda provided with the meeting. The meeting type may be obtained from identifying one or more predetermined keywords or by employing NLP techniques.

In some examples, the video conference provider 310 may instead (or also) request the host select a meeting type or sub-type for the meeting. For example, in a medical setting, the video conference provider 310 may request that the meeting host, e.g., a doctor or other medical staff, identify the type of appointment, e.g., annual checkup, pre-surgical meeting, follow-up appointment, etc. Once the meeting type is selected, the video conference provider 310 may request further details, e.g., as a meeting sub-type. Such additional information may indicate a specific reason for the medical appointment, such as pre-surgical meeting relating to a gall bladder surgery, an appendectomy, etc. Similarly, additional information about a follow-up appointment may be requested, such as the reason for the follow-up, e.g., to review test results, post-surgical follow-up, etc. Additional types of information may be provided as well, such as whether the meeting is with a patient or client, or is an internal meeting with another employee. And while these examples are given in the medical context, they are applicable to any context, e.g., education, corporate, employment, etc. Thus, meeting types may include parent-teacher conferences, quarterly financial reviews, performance reviews, new employee hires or training, etc.

At block 720, the video conference provider 310 obtains multimedia content associated with the meeting type. To obtain the multimedia content, the video conference provider 310 may access a data store having multimedia content and retrieving a multimedia content item (or "content item") associated with the meeting content. For example, when the host scheduled the meeting, or any time before the meeting begins, the meeting host may provide multimedia content associated with the meeting to be provided participants that enter a waiting room for the meeting. The video conference provider 310 receives the multimedia content item from the host and stores it in a data store, and associates it with the meeting.

However, in some examples, the host, or an organization associated with the host (e.g., a company, a doctor's office, a school, a governmental agency, etc.), may provide multiple multimedia content items to the video conference provider 310 whose subject matter may be associated with a number of different meeting types or sub-types that are commonly scheduled by the host or organization. Such content items may have titles that indicate the subject matter of the respective content item, or they may include metadata, e.g., one or more metadata tags or fields, indicating the subject matter of the content item. It should be appreciated that multiple content items related to the same subject matter may be provided, e.g., multiple videos related to a particular medical procedure. Such content items may have differing lengths or levels of detail, one or which may be suitable for a patient while another may be suitable for medical staff. Further, in some examples, information about the host or the participant may be used to select or otherwise obtain a suitable multimedia content item. Thus, in some examples, the content items may include metadata or other information indicating the target audience for the content item, e.g., for a patient, client, employee, etc.

Obtaining a multimedia content item may involve searching for suitable content items amongst a corpus of available content items, as suggested above. For example, the video conference provider 310 may have a large library of content items for a particular organization, e.g., a medical practice. The library may include videos, forms, surveys, games, exercises, etc. Thus, the video conference provider 310 may employ different criteria to select a content item in different examples. In another example, the video conference provider 310 may access a third-party content provider 330, e.g., an online, publicly available, video service, a company contracted to provide content items to the video conference provider 310 (or with whom the video conference provider has a subscription or other agreement), etc., to search for relevant multimedia content.

For example, the video conference provider 310 may determine an expected time that a participant will be waiting in the waiting room. For example, a meeting may be scheduled to begin at 2 pm; however, the patient may be instructed to join 15 minutes early to review forms or video content to prepare them for the subject matter of the meeting. Alternatively, the meeting may be scheduled to begin at 2 pm, but the meeting host may provide additional information tot eh video conference provider indicating that the host will join at 2:10 pm (or some other time after the scheduled start time) to provide the participant(s) with an opportunity to review any content item(s) to be presented. Thus, the video conference provider 310 may select a content item associated with the meeting type or sub-type and based on the expected wait time and duration of the content item.

In some examples, the video conference provider 310 may select a content item based on past history for other meetings having similar meeting types of sub-types. For example, a meeting host may identify certain content items for a particular meeting. At a later date, the meeting host may schedule a meeting relating to the same subject matter with a different participant. The video conference provider 310 may search for past meetings scheduled by the host, identify past meetings having similar types or sub-types, and then identify content items that were selected for such meetings.

Additional criteria may be used to select a content item, such as viewer ratings of one or more content items associated with the meeting type of sub-type may be employed. Thus, the video conference provider 310 may select a content item having the highest viewer rating, or it may only select content items having a viewer rating about a threshold value. In some examples, the content item may have an indicator of an expected skill level or understanding level of the viewer, e.g., novice, expert, etc., or patient, health care provider, etc. Such information may be included as discussed above, e.g., in the title of the content item ("advanced suturing techniques" versus "do's and don'ts when you have stitches"). Thus, in some examples, the content may be selected based on the type of participant, e.g., a medical student versus a patient, or the host, e.g., a professor versus a doctor.

In some examples, one or more forms or questionnaires may be selected based on form type, e.g., forms for new patients, forms related to employee evaluations, etc. Thus, the video conference provider 310 may search both for video (or other such content) as well as forms. If one or more suitable forms is identified, the forms may be selected.

The video conference provider 310 may use any such criteria described above to select one or more suitable content items. If multiple potential content items are selected, the video conference provider 310 may then one specific content item based on any suitable technique, e.g., scoring the content items based on the qualities of their respective criteria (e.g., how closely does the run-time of a video match the expected wait time, viewer ratings of 4.5 versus 4.8, etc.). Depending on the meeting type, multiple content items may be selected for presentation to the participant. For example, if multiple forms are associated with the meeting type, the video conference provider 310 may select all of the forms. Still other techniques may be used according to different examples.

At block 730, the video conference provider 310 receives a request to join a main meeting of a video conference from a client device. As discussed above, a participant may employ their client device, e.g., client device 340, to request to join a meeting.

At block 740, the video conference provider 310 connects the client device 340 to a waiting room, e.g., waiting room 450 (which may be the main meeting, e.g., main meeting 432, as discussed above). As discussed above, the meeting host may configure the video conference to require participants to be placed into a waiting room. In some examples, the video conference provider 310 may automatically always connect participants to waiting rooms, or may do so if the meeting host has not connected to the main meeting.

At block 750, the video conference provider 310 the selected multimedia content item(s) to the client device in the waiting room. In one example, the content item may be provided in one or more multimedia streams to the client device 340. Such multimedia streams may be provided generally as described above with respect to FIGS. 1-3. If multiple content items have been selected for presentation, the video conference provider 310 may provide them serially, such as by beginning a content item after prior content item has finished. It should be appreciated that in some examples, a multimedia content item, such as a form, may be provided as a dialog box or within a window in a GUI provided by the video conference software executed by the client device 340.

At block 760, the video conference provider 310 receives information responsive to one or more fields in a questionnaire (or form) or other interactive multimedia content. As discussed above, if the video conference provider 310 selects a form or other interactive multimedia content item to provide to the participant in the waiting room. In response, the participant may provide responses to one or more questions in the form or may provide input to the interactive multimedia content. The video conference provider 310 receives the information (e.g., selections, free-form text, or other inputs) from the client device 340 and associates it with the main meeting, such as by storing the information in a data store at the video conference provider 310.

At block 770, the video conference provider 310 provides the received information from block 760 to the meeting host. For example, the video conference provider 310 may transmit one or more documents to the meeting host via email, or it may provide the responses or other inputs in a window in the GUI presented to the meeting host. This may then allow the meeting host to review the information provided by the participant before or during the meeting, if needed.

It should be appreciated that the method 700 described above was described in a particular order, but no specific order is required. For example, block 710 or 720 may be performed after the client device 340 has been connected to the waiting room.

Figure 8:
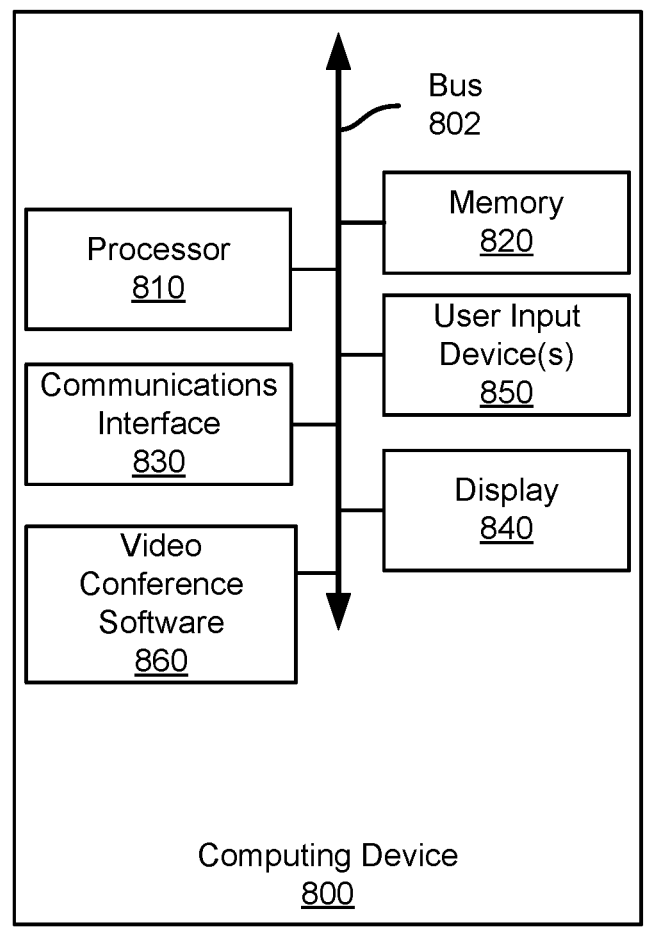
FIG. 8 shows an example computing device suitable for use with systems and methods for providing dynamic content to video conference waiting rooms.

Referring now to FIG. 8, FIG. 8 shows an example computing device 800 suitable for use in example systems or methods for providing dynamic content to video conference waiting rooms according to this disclosure. The example computing device 800 includes a processor 810 which is in communication with the memory 820 and other components of the computing device 800 using one or more communications buses 802. The processor 810 is configured to execute processor-executable instructions stored in the memory 820 to perform one or more methods for providing dynamic content to video conference waiting rooms according to different examples, such as part or all of the example method 700 described above with respect to FIG. 7. The computing device 800, in this example, also includes one or more user input devices 850, such as a keyboard, mouse, touchscreen, microphone, etc., to accept user input. The computing device 800 also includes a display 840 to provide visual output to a user.

In addition, the computing device 800 includes video conference software 860 to enable a user to join and participate in a video conference, such as a conventional meeting or webinar, by receiving multimedia streams from a video conference provider, sending multimedia streams to the video conference provider, joining and leaving breakout rooms, such as described throughout this disclosure, etc.

The computing device 800 also includes a communications interface 840. In some examples, the communications interface 830 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
receiving, by a video conference provider, an indication of content discussed within a video conference;
selecting, by the video conference provider, a multimedia content item from a plurality of available multimedia content items based on the content;
receiving a request from a client device to join a main meeting of the video conference;
connecting the client device to a waiting room associated with the video conference; and
providing the multimedia content item to the client device in the waiting room.

2. The method of claim 1, wherein receiving the indication of the content discussed within the meeting comprises determining a title of the meeting, a description of the meeting, or a description of a class associated with the meeting.

3. The method of claim 1, wherein obtaining the multimedia content comprises:
accessing a data store having a plurality of multimedia content items and corresponding descriptions, and
selecting a multimedia content item of the plurality of multimedia content items based on the indication of the content discussed within the video conference and metadata corresponding to the multimedia content items.

4. The method of claim 1, wherein providing the multimedia content comprises providing a video or audio stream associated with the selected multimedia content.

5. The method of claim 3, further comprising selecting the multimedia content based on a rating of the multimedia content.

6. The method of claim 3, further comprising selecting the multimedia content based on a duration of the multimedia content and an estimated wait time.

7. The method of claim 1, wherein the multimedia content comprises one or more forms, and further comprising:
receiving, from the client device, information responsive to one or more fields in the one or more forms; and
storing the received information in one or more data store records.

8. The method of claim 1, further comprising:
receiving a plurality multimedia content items from a client device; and wherein obtaining the multimedia content comprises obtaining the multimedia content from the plurality of multimedia content items.

9. A system comprising:
a communications interface;
a non-transitory computer-readable medium; and
one or more processors configured to execute processor-executable instructions stored in the non-transitory computer-readable medium to:
receive an indication of content discussed within a video conference;
select a multimedia content item from a plurality of available multimedia content items based on the content;
receive a request from a client device to join a main meeting of the video conference;
connect the client device to a waiting room associated with the video conference; and
provide the multimedia content item to the client device in the waiting room.

10. The system of claim 9, wherein the one or more processors are configured to execute further processor-executable instructions stored in the non-transitory computer-readable medium to determine a title of the meeting, a description of the meeting, or a description of a class associated with the meeting.

11. The system of claim 9, wherein the one or more processors are configured to execute further processor-executable instructions stored in the non-transitory computer-readable medium to:
access a data store having a plurality of multimedia content items and corresponding descriptions, and
select a multimedia content item of the plurality of multimedia content items based on the indication of content discussed within a video conference and metadata corresponding to the multimedia content items.

12. The system of claim 9, wherein the one or more processors are configured to execute further processor-executable instructions stored in the non-transitory computer-readable medium to provide a video or audio stream associated with the selected multimedia content.

13. The system of claim 12, wherein the one or more processors are configured to execute further processor-executable instructions stored in the non-transitory computer-readable medium to select the multimedia content based on a rating of the multimedia content.

14. The system of claim 12, wherein the one or more processors are configured to execute further processor-executable instructions stored in the non-transitory computer-readable medium to select the multimedia content based on a duration of the multimedia content and an estimated wait time.

15. The system of claim 9, wherein the multimedia content comprises one or more forms, and wherein the one or more processors are configured to execute further processor-executable instructions stored in the non-transitory computer-readable medium to:
receive, from the client device, information responsive to one or more fields in the one or more forms; and
store the received information in one or more data store records.

16. The system of claim 9, wherein the one or more processors are configured to execute further processor-executable instructions stored in the non-transitory computer-readable medium to:
receive a plurality multimedia content items from a client device;
and obtain the multimedia content from the plurality of multimedia content items.

17. A non-transitory computer-readable medium comprising processor-executable instructions configured to cause one or more processors to:
receive an indication of content discussed within a video conference;
select a multimedia content item from a plurality of available multimedia content items based on the content;
receive a request from a client device to join a main meeting of the video conference;
connect the client device to a waiting room associated with the video conference; and
provide the multimedia content item to the client device in the waiting room.

18. The non-transitory computer-readable medium of claim 17, further comprising processor-executable instructions configured to cause one or more processors to determine a title of the meeting, a description of the meeting, or a description of a class associated with the meeting.

19. The non-transitory computer-readable medium of claim 17, further comprising processor-executable instructions configured to cause one or more processors to:
- access a data store having a plurality of multimedia content items and corresponding descriptions, and
- select a multimedia content item of the plurality of multimedia content items based on the indication of content discussed within a video conference and metadata corresponding to the multimedia content items.

20. The non-transitory computer-readable medium of claim 17, further comprising processor-executable instructions configured to cause one or more processors to provide a video or audio stream associated with the selected multimedia content.

* * * * *